US008591500B2

(12) United States Patent
Naito

(10) Patent No.: US 8,591,500 B2
(45) Date of Patent: Nov. 26, 2013

(54) TREATMENT APPARATUS

(75) Inventor: Kimihiko Naito, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/483,816

(22) Filed: May 30, 2012

(65) Prior Publication Data

US 2012/0303003 A1    Nov. 29, 2012

Related U.S. Application Data

(63) Continuation of application No. PCT/JP2011/073419, filed on Oct. 12, 2011.

(30) Foreign Application Priority Data

Oct. 28, 2010 (JP) .................................. 2010-242135

(51) Int. Cl.
*A61B 17/00* (2006.01)
(52) U.S. Cl.
USPC ................ 606/1; 606/130; 606/205; 606/206
(58) Field of Classification Search
None
See application file for complete search history.

(56) References Cited

U.S. PATENT DOCUMENTS

| 5,439,478 A * | 8/1995 | Palmer ........................... 606/205 |
| 6,569,105 B1 * | 5/2003 | Kortenbach et al. ........... 600/562 |
| 2005/0004432 A1 | 1/2005 | Suzuki et al. |
| 2005/0096694 A1 | 5/2005 | Lee |
| 2009/0024141 A1 | 1/2009 | Stahler et al. |

FOREIGN PATENT DOCUMENTS

| JP | A-2005-34623 | 2/2005 |
| JP | A-2007-509698 | 4/2007 |
| JP | A-2009-142513 | 7/2009 |

OTHER PUBLICATIONS

International Search Report issued in International Application No. PCT/JP2011/073419 dated Nov. 8, 2011 (with translation).
Jan. 28, 2013 Supplementary Search Report issued in European Patent Application 11 83 6023.
May 23, 2013 International Preliminary Report on Patentability issued in International Application No. PCT/JP2011/073419 (translation only).
Nov. 8, 2011 Written Opinion of the International Searching Authority issued in International Application No. PCT/JP2011/073419 (translation only).

* cited by examiner

*Primary Examiner* — Bill Thomson
*Assistant Examiner* — Lynsey Crandall
(74) *Attorney, Agent, or Firm* — Oliff & Berridge, PLC

(57) ABSTRACT

A rotor of a treatment apparatus includes a first outer surface spaced apart from the longitudinal directions axis of a flexible tube section by a first distance in radial directions, and a second outer surface spaced apart from the longitudinal directions axis of the flexible tube section by a second distance smaller than the first distance in the radial directions. The treatment apparatus includes a first rotating operation wire extending from a wire fixing portion to the first outer surface, a second rotating operation wire extending from the wire fixing portion to the second outer surface, and a wire intersecting portion in which the first and second rotating operation wires intersect at positions apart from each other in a state that the second rotating operation wire is located on an inner direction side of the first rotating operation wire.

6 Claims, 10 Drawing Sheets

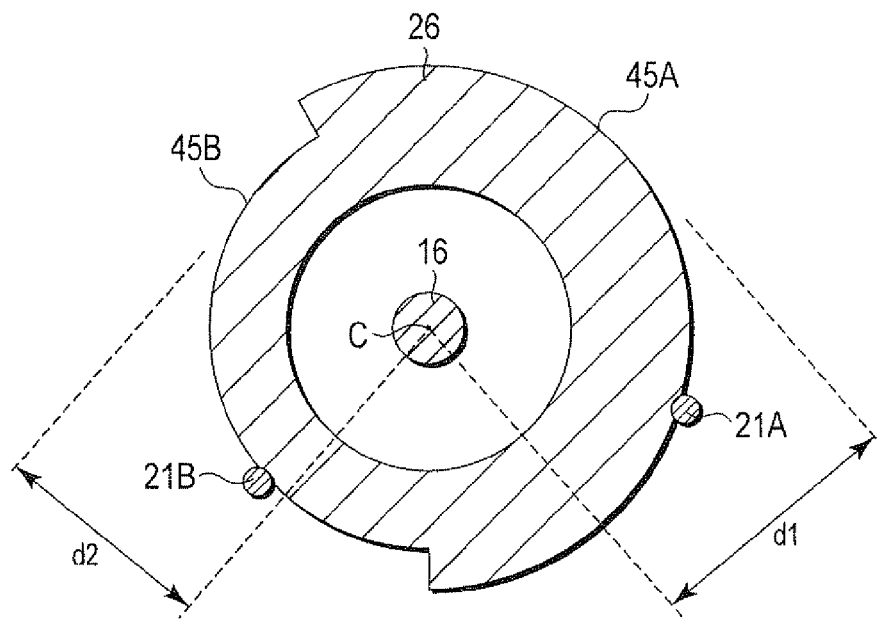
F I G. 11
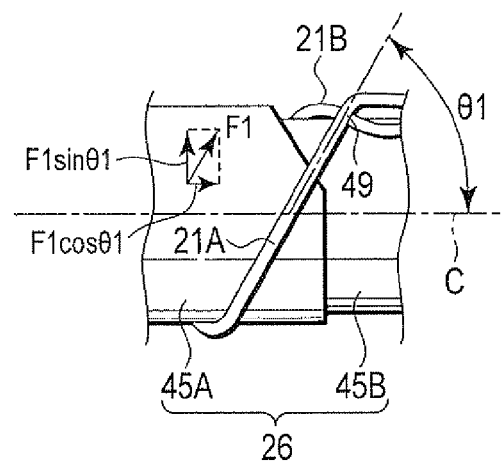
F I G. 12

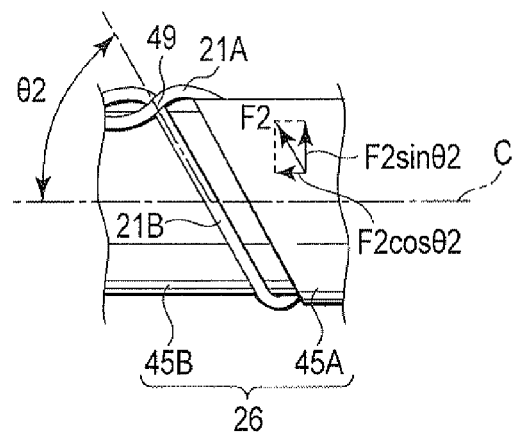
F I G. 13
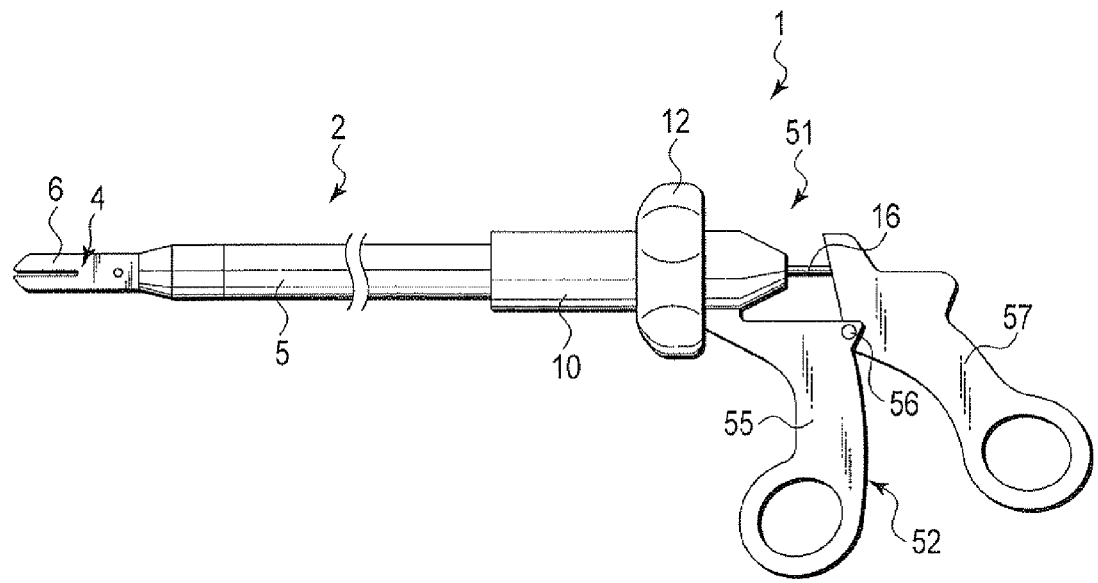
F I G. 14

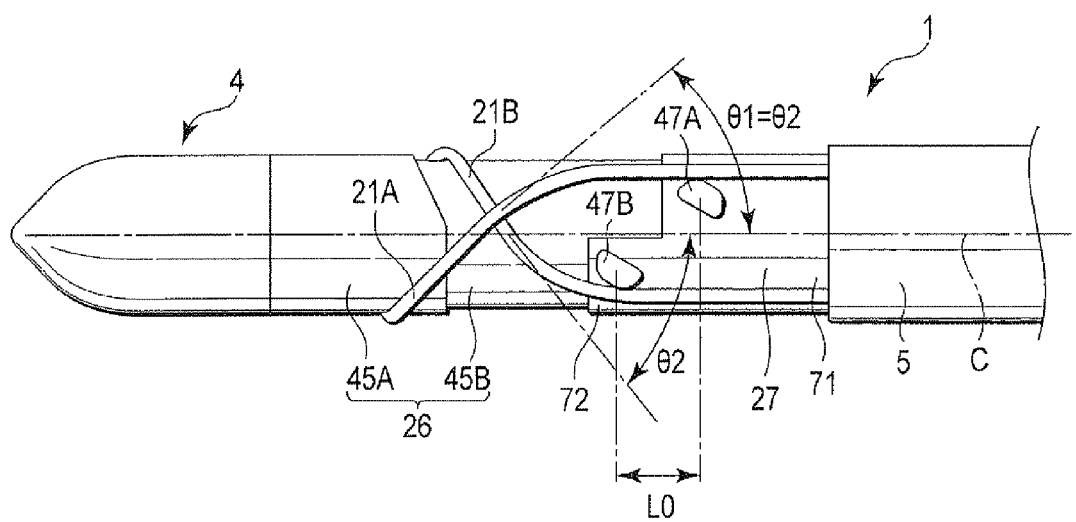
F I G. 17

TREATMENT APPARATUS

CROSS-REFERENCE TO RELATED APPLICATIONS

This is a Continuation Application of PCT Application No. PCT/JP2011/073419, filed Oct. 12, 2011 and based upon and claiming the benefit of priority from prior Japanese Patent Application No. 2010-242135, filed Oct. 28, 2010, the entire contents of which are incorporated herein by reference.

BACKGROUND OF THE INVENTION

1. Field of the Invention

The present invention relates to a treatment apparatus such as forceps or a manipulator which is configured to be inserted into the body cavity of a patient to treat a morbid section.

2. Description of the Related Art

Jpn. Pat. Appln. KOKAI Publication No. 2009-142513 discloses a high-frequency treatment apparatus which is configured to grip a morbid section with high-frequency electrodes to treat the morbid section. This high-frequency treatment apparatus includes an insertion section configured to be inserted into a body cavity, and an operation section provided to a proximal direction side of the insertion section. The insertion section includes a distal treatment section provided with high-frequency electrodes, and a flexible tube section which is provided to the proximal direction side of the distal treatment section and extends in longitudinal directions. When rotating the distal treatment section, the operator rotates the operation section to transfer rotational torque to the distal treatment section via a conductive line serving as a rotating operation transfer member extending through the flexible tube section. With this operation, the distal treatment section rotates to directions around an axis relative to the flexible tube section.

BRIEF SUMMARY OF THE INVENTION

According to one aspect of the invention, a treatment apparatus includes that a flexible tube section which has a longitudinal directions axis and extends in longitudinal directions; a distal treatment section which is provided to a distal direction side of the flexible tube section, and which is configured to rotate to directions about an axis relative to the flexible tube section; a rotating operation section which is provided to a proximal direction side of the flexible tube section, and which is configured to perform rotating operation of the distal treatment section; a rotor which is fixed to the distal treatment section between the distal treatment section and the flexible tube section, and which is configured to rotate to the directions about the axis relative to the flexible tube section, the rotor including a first outer surface spaced apart from the longitudinal directions axis of the flexible tube section by a first distance in radial directions, and a second outer surface spaced apart from the longitudinal directions axis of the flexible tube section by a second distance smaller than the first distance in the radial directions; a wire fixing portion which is provided to the rotor or a portion to the distal direction side of the rotor; a first rotating operation wire which has a distal end fixed to the wire fixing portion and extends from the wire fixing portion to the first outer surface of the rotor, the first rotating operation wire being configured to be moved by the rotating operation section in an extending direction to rotate the distal treatment section and the rotor in a first rotation direction; a second rotating operation wire which has a distal end fixed to the wire fixing portion and extends from the wire fixing portion to the second outer surface of the rotor, the second rotating operation wire being configured to be moved by the rotating operation section in an extending direction to rotate the distal treatment section and the rotor in a second rotation direction opposite to the first rotation direction; and a wire intersecting portion in which the first rotating operation wire and the second rotating operation wire intersect each other at positions apart from each other in a state that the second rotating operation wire is located on an inner direction side of the first rotating operation wire.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 11 is a sectional view taken along a line II-II in FIG. 7;

FIG. 12 is a schematic view explaining the rotating movement of the distal treatment section of the treatment apparatus according to the first embodiment in the first rotation direction;

FIG. 13 is a schematic view explaining the rotating movement of the distal treatment section of the treatment apparatus according to the first embodiment in the second rotation direction;

FIG. 14 is a schematic view of a treatment apparatus according to the first modification of the first embodiment;

FIG. 17 is a plan view schematically showing the configuration of the distal direction side part of a treatment apparatus according to the second embodiment of the present invention.

DETAILED DESCRIPTION OF THE INVENTION (First Embodiment)

The first embodiment of the present invention will be described with reference to FIGS. 1 to 13.

Figure 1:
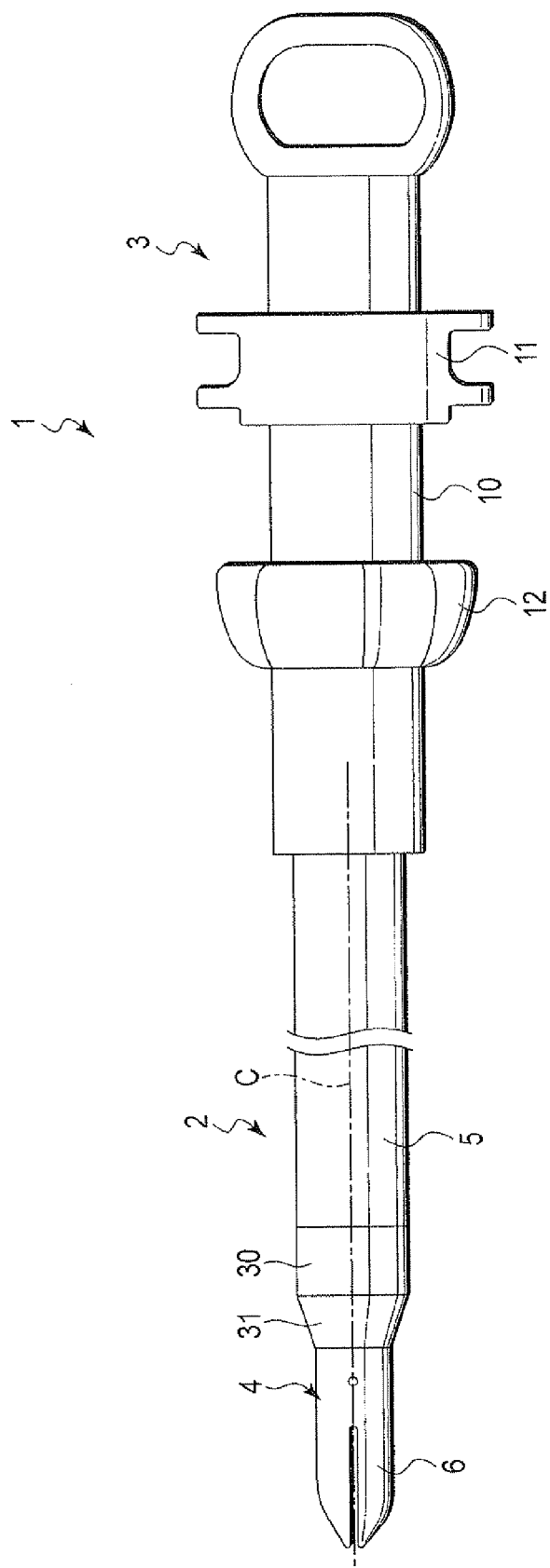
FIG. 1 is a schematic view showing a treatment apparatus according to the first embodiment of the present invention.

FIG. 1 is a view showing the configuration of a treatment apparatus 1 according to this embodiment. As shown in FIG. 1, the treatment apparatus 1 includes an insertion section 2 configured to be inserted into a body cavity, and an operation section 3 provided to a proximal direction side of the insertion section 2. The insertion section 2 includes a distal treatment section 4 configured to perform treatment, and a flexible tube section 5 which is provided to the proximal direction side of the distal treatment section 4 and extends in longitudinal directions. The distal treatment section 4 is provided with a grip portion 6 configured to grip a tissue or the like. The flexible tube section 5 has a longitudinal directions axis C.

Figure 2:
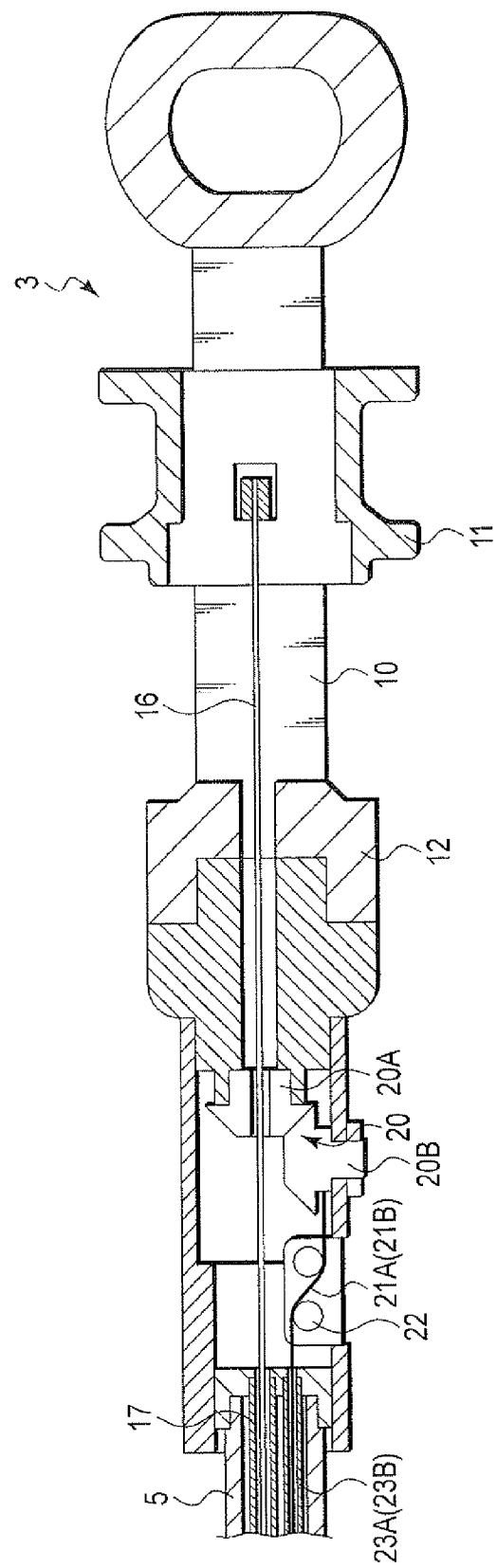
FIG. 2 is a sectional view schematically showing the configuration of the operation section of the treatment apparatus according to the first embodiment.

FIG. 2 is a view showing the configuration of the operation section 3. As shown in FIG. 2, the operation section 3 includes an operation section main body 10, a grip operation handle 11 serving as a grip operation section which is configured to perform the grip operation of gripping a tissue or the like with the grip portion 6, and a rotating operation handle 12 serving as a rotating operation section which is configured to perform the rotating operation of rotating the distal treatment section 4 to directions about the axis relative to the flexible tube section 5.

The grip operation handle 11 is mounted on the operation section main body 10 so as to be movable in the longitudinal directions relative to the operation section main body 10. The proximal end of a grip operation wire 16 serving as a grip operation transfer member, which is configured to transfer grip operation to the grip portion 6, is fixed to the grip operation handle 11. The distal end of the grip operation wire 16 is connected to the grip portion 6 of the distal treatment section 4 through the interior of the flexible tube section 5. Inside the flexible tube section 5, the grip operation wire 16 extends through a coil pipe 17 used in grip operation. The grip operation wire 16 is pulled or loosened by moving the grip operation handle 11 relative to the operation section main body 10 in the longitudinal directions.

The rotating operation handle 12 is mounted on the operation section main body 10 so as to be rotatable to the directions around the axis relative to the operation section main body 10. A bevel gear 20 is coupled to the rotating operation handle 12. The bevel gear 20 includes a first gear 20A coupled to the rotating operation handle 12, and a second gear 20B meshed with the first gear 20A. The proximal ends of first and second rotating operation wires 21A and 21B serving as rotating operation transfer members, which is configured to transfer rotating operation to the distal treatment section 4, are connected to the second gear 20B. The first and second rotating operation wires 21A and 21B are guided into the flexible tube section 5 by guide pulleys 22, and extend in almost longitudinal directions inside the flexible tube section 5. Inside the flexible tube section 5. Each of the first and second rotating operation wires 21A and 21B extends through corresponding coil pipe 23A and 23B used in rotating operation. For example, the first rotating operation wire 21A extends through the coil pipe 23A. When the rotating operation handle 12 is rotated to directions about the axis, the first gear 20A of the bevel gear 20 rotates together with the rotating operation handle 12 to directions about (around) the axis. As the first gear 20A rotates, the second gear 20B rotates about an axis perpendicular to the longitudinal directions. As the second gear 20B rotates in one rotation direction, the first rotating operation wire 21A is pulled, and the second rotating operation wire 21B is loosened. As the second gear 20B rotates in the other rotation direction, the first rotating operation wire 21A is loosened, and the second rotating operation wire 21B is pulled.

Figure 3:
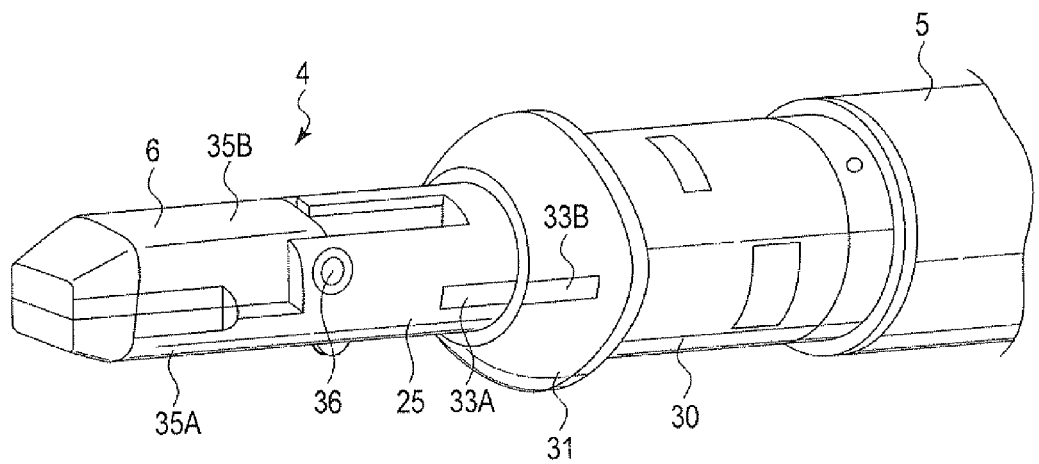
FIG. 3 is a perspective view schematically showing the configuration of a distal direction side part of the treatment apparatus according to the first embodiment.
Figure 4:
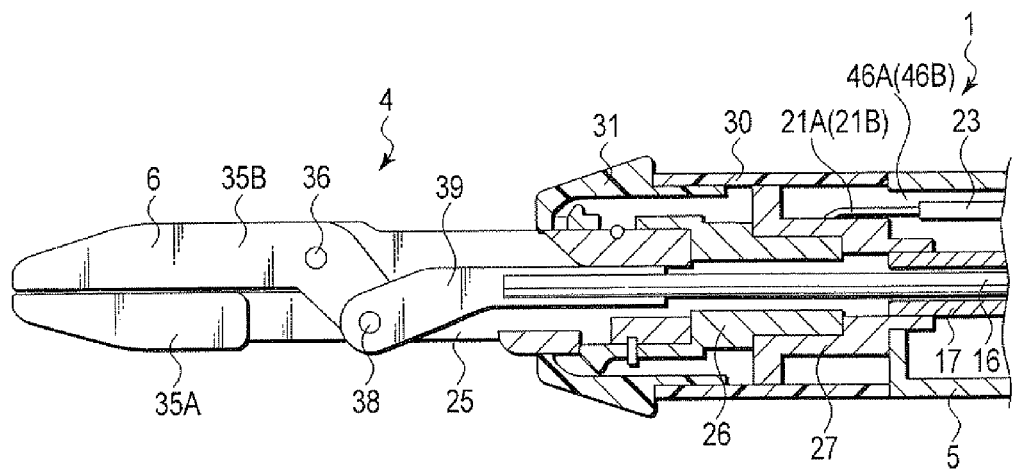
FIG. 4 is a sectional view schematically showing the configuration of the distal direction side part of the treatment apparatus according to the first embodiment.

FIGS. 3 and 4 are views showing the configuration of a distal direction side part of the treatment apparatus 1. As shown in FIGS. 3 and 4, a rotor 26 is fixed to the distal treatment section 4 between the distal treatment section 4 and the flexible tube section 5. A rotor support member 27 is provided between the rotor 26 and the flexible tube section 5. The rotor support member 27 is fixedly coupled to the flexible tube section 5. The rotor 26 is coupled to the rotor support member 27 so as to be rotatable to directions about the axis. A first cover 30 having a cylindrical shape is provided to an outer direction side of the rotor support member 27. The first cover 30 is fixedly coupled to the flexible tube section 5. A second cover 31 having a circular truncated cone cylindrical shape is provided to the distal direction side of the first cover 30 so as to be fixed to the first cover 30. This configuration allows the distal treatment section 4 and the rotor 26 to rotate together to directions about the axis relative to the flexible tube section 5, the rotor support member 27, the first cover 30, and the second cover 31.

Note that as shown in FIG. 3, a first index 33A may be provided on an outer surface of the distal treatment section 4, and a second index 33B may be provided on an outer surface of the second cover 31. This makes the operator check the positional relationship between the first index 33A and the second index 33B from an image of an endoscope or the like used together with the treatment apparatus 1. The positional relationship between the first index 33A and the second index 33B allows the operator to recognize the neutral position (initial position) of the distal treatment section 4 and the amount of rotation of the distal treatment section 4 to the directions about the axis relative to the flexible tube section 5.

As shown in FIGS. 3 and 4, the distal treatment section 4 includes a treatment section main body 25. A distal direction side part of the treatment section main body 25 is provided with a first clamping portion 35A of the grip portion 6. A second clamping portion 35B of the grip portion 6 is pivotably supported by the treatment section main body 25 through a coupling pin 36. The second clamping portion 35B can rotate together with the treatment section main body 25 to the directions about the axis relative to the flexible tube section 5. The second clamping portion 35B can pivot about the coupling pin 36 relative to the treatment section main body 25. As the second clamping portion 35B pivots relative to the treatment section main body 25, the second clamping portion 35B opens and closes relative to the first clamping portion 35A of the treatment section main body 25.

As shown in FIG. 4, the coil pipe 17 used in grip operation, through which the grip operation wire 16 extends, extends through the flexible tube section 5 and is coupled to the rotor support member 27 with the distal end of the coil pipe 17 being fixed to the rotor support member 27. The grip operation wire 16 extends to the distal direction side of the distal end of the coil pipe 17. Inside the treatment section main body 25, a coupling member 39 coupled to the second clamping portion 35B through a coupling pin 38 is provided. The grip operation wire 16 extends through the rotor support member 27 and the rotor 26, and has its distal end fixed to the coupling member 39. With this configuration, when the grip operation wire 16 is pulled or loosened by operating the grip operation handle 11, the coupling member 39 moves in the longitudinal directions in accordance with the pulling or loosening of the grip operation wire 16. As the coupling member 39 moves, the second clamping portion 35B pivots about the coupling pin 36 relative to the treatment section main body 25. As the coupling member 39 moves to the distal direction, the second clamping portion 35B pivots in a direction to open relative to the first clamping portion 35A. In contrast, as the coupling member 39 moves to the proximal direction, the second clamping portion 35B pivots in a direction to close relative to the first clamping portion 35A.

Note that in the treatment apparatus 1, since the coil pipe 17 used with a grip operation wire is coupled to the rotor support member 27, when the rotor 26 rotates, only the grip operation wire 16 rotates, but the coil pipe 17 does not rotate. For this reason, the rotational torque that rotates the rotor 26 decreases as compared with the case in which the coil pipe 17 rotates together with the rotor 26.

Figure 9:
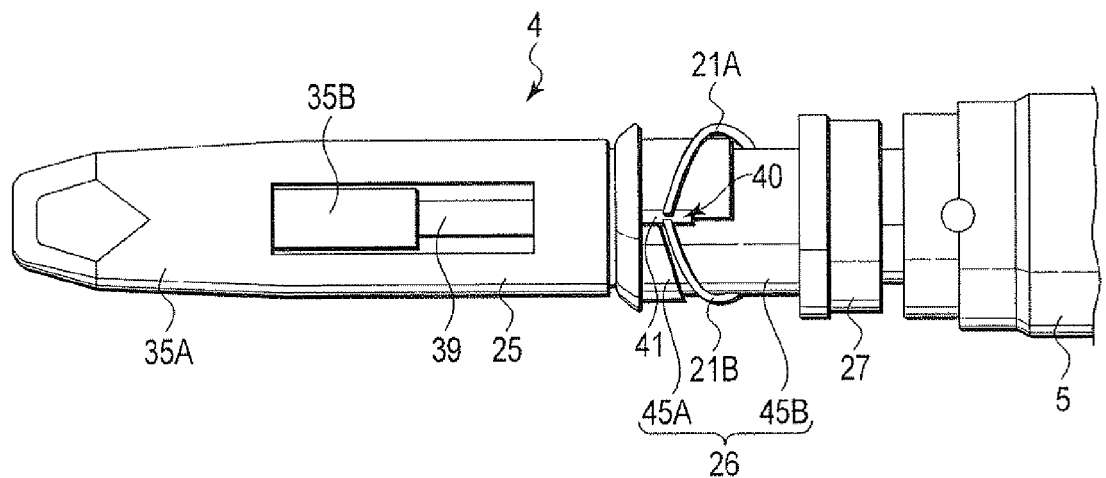
FIG. 9 is a bottom view schematically showing the distal direction side part of the treatment apparatus according to the first embodiment with the first cover and second cover being removed.

FIGS. 5 to 9 are views showing the configuration of the distal direction side part of the treatment apparatus 1 from which the first and second covers 30 and 31 are removed. As shown in FIG. 9, the distal direction side part of the rotor 26 is provided with a through hole 41 extending through the rotor 26 in radial directions.

Figure 10:
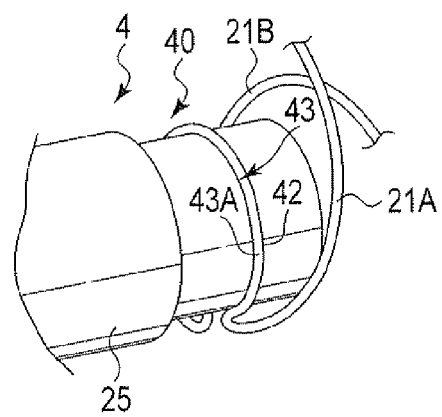
FIG. 10 is a perspective view schematically showing the configuration of a wire fixing portion, to which the distal ends of the first and second rotating operation wires of the treatment apparatus according to the first embodiment are fixed.

FIG. 10 is a view showing the configuration of a wire fixing portion 40 which is configured to fix the distal ends of the first and second rotating operation wires 21A and 21B. As shown in FIG. 10, the coupling portion between the treatment section main body 25 (distal treatment section 4) and the rotor 26 is provided with a groove portion 42 along the circumferential directions. One linear member 43 is fixed to the groove portion 42 in a wound state by brazing or the like to form a winding portion 43A. The linear member 43 extends from the two ends of the winding portion 43A to the outer direction side of the rotor 26 through the through hole 41. A portion of the linear member 43 which extends from one end of the winding portion 43A to the outer direction side of the rotor 26 forms the first rotating operation wire 21A. A portion of the linear member 43 which extends from the other end of the winding portion 43A to the outer direction side of the rotor 26 forms the second rotating operation wire 21B.

In this embodiment, the first and second rotating operation wires 21A and 21B are formed from the single linear member 43 in consideration of efficiency in the assembly operation of a treatment apparatus. However, the embodiment is not limited to this. For example, the first and second rotating operation wires 21A and 21B may be formed from two different linear members, and each of the linear members is fixed to the groove portion 42 of the distal treatment section 4.

The outer surface of the rotor support member 27 is provided with a first convex portion 47A and a second convex portion 47B which protrude in the outer direction. The first convex portion 47A is disposed at a position apart from the through hole 41 of the rotor 26 in the circumferential directions. The second convex portion 47B is located at a position apart from the through hole 41 of the rotor 26 in the circumferential directions toward a direction opposite to a direction toward the first convex portion 47A. The first and second convex portions 47A and 47B are located at almost the same position in the longitudinal directions. The distance from the longitudinal directions axis C of the flexible tube section 5 to the root portion of the first convex portion 47A in the radial directions is almost equal to the distance from the longitudinal directions axis C of the flexible tube section 5 to the root portion of the second convex portion 47B in the radial directions. A portion of the rotor support member 27, which is located to the proximal direction side of the first convex portion 47A (second hole portion 47B), is provided with a first hole portion 46A and a second hole portion 46B.

Figure 7:
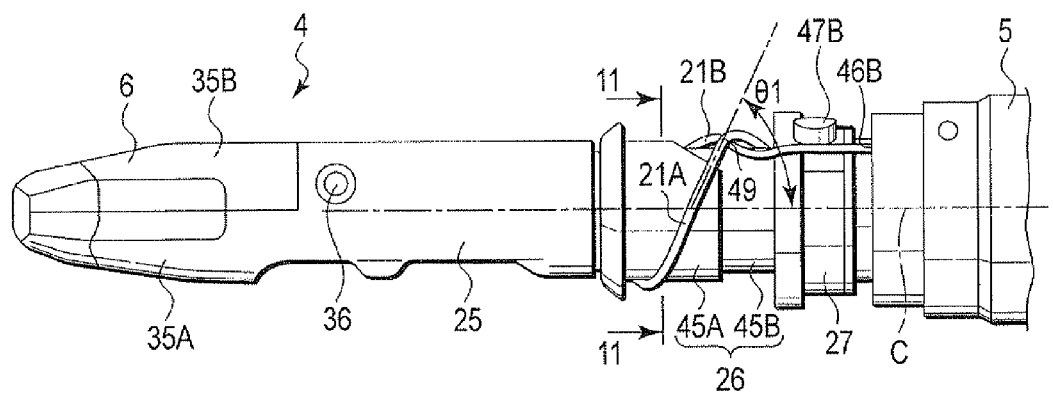
FIG. 7 is a side view taken from a direction of an arrow A in FIG. 6, which schematically shows the distal direction side part of the treatment apparatus according to the first embodiment with the first cover and second cover being removed.
Figure 8:
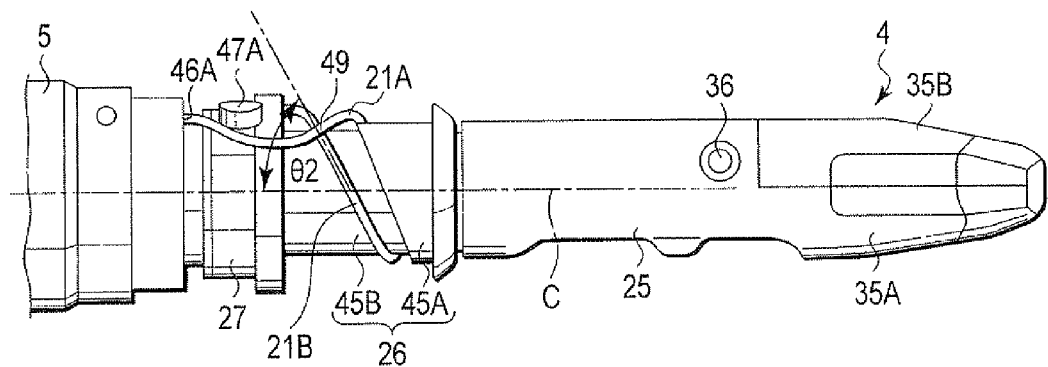
FIG. 8 is a side view taken from a direction of an arrow B in FIG. 6, which schematically shows the distal direction side part of the treatment apparatus according to the first embodiment with the first cover and second cover being removed.

FIG. 11 is a sectional view taken along a line 11-11 in FIG. 7. As shown in FIGS. 9 and 11, the rotor 26 includes a first outer surface 45A spaced apart from the longitudinal directions axis C of the flexible tube section 5 by a first distance d1 in the radial directions, and a second outer surface 45B spaced apart from the longitudinal directions axis C of the flexible tube section 5 by a second distance d2 smaller than the first distance d1 in the radial directions. The difference between the first distance d1, which is the distance from the longitudinal directions axis C of the flexible tube section 5 to the first outer surface 45A in the radial directions, and the second distance d2, which is the distance from the longitudinal directions axis C of the flexible tube section 5 to the second outer surface 45B in the radial directions, is equal to or more than a diameter of the second rotating operation wire 21B.

As shown in FIGS. 5 to 9, the first rotating operation wire 21A, extending from the wire fixing portion 40 in the outer direction, extends to the first outer surface 45A of the rotor 26 along a first oblique direction inclining from the longitudinal directions to the circumferential directions. The first rotating operation wire 21A, extending to the first outer surface 45A, abuts against the first convex portion 47A of the rotor support member 27. When the first rotating operation wire 21A abuts against the first convex portion 47A, an extending direction of the first rotating operation wire 21A is changed from the first oblique direction. The first rotating operation wire 21A is inserted from the first hole portion 46A into the flexible tube section 5. The first rotating operation wire 21A, inserted in the flexible tube section 5, extends to the rotating operation section (rotating operation handle 12). Assume that the angle between the longitudinal directions and the first oblique direction is defined as a first angle $\theta 1$ (see FIG. 7).

The second rotating operation wire 21B, extending from the wire fixing portion 40 in the outer direction, extends to the second outer surface 45B of the rotor 26 along a second oblique direction inclining from the longitudinal directions to the circumferential directions toward a direction opposite to a direction toward the first oblique direction. The second rotating operation wire 21B, extending to the second outer surface 45B, abuts against the second convex portion 47B of the rotor support member 27. The second rotating operation wire 21B abuts against the second convex portion 47B to change an extending direction of the second rotating operation wire 21B from the second oblique direction. The second rotating operation wire 21B is inserted from the second hole portion 46B into the flexible tube section 5. The second rotating operation wire 21B, inserted in the flexible tube section 5, extends to the rotating operation section (rotating operation handle 12). Assume that the angle between the longitudinal directions and the second oblique direction is defined as a second angle $\theta 2$ (see FIG. 8).

As described above, the second distance d2 from the longitudinal directions axis C of the flexible tube section 5 to the second outer surface 45B in the radial directions is smaller than the first distance d1 from the longitudinal directions axis C of the flexible tube section 5 to the first outer surface 45A in the radial directions. In addition, the first and second convex portions 47A and 47B are located at almost the same position in the longitudinal directions. For this reason, the first angle θ1 between the longitudinal directions and the first oblique direction is larger than the second angle θ2 between the longitudinal directions and the second oblique direction.

Figure 5:
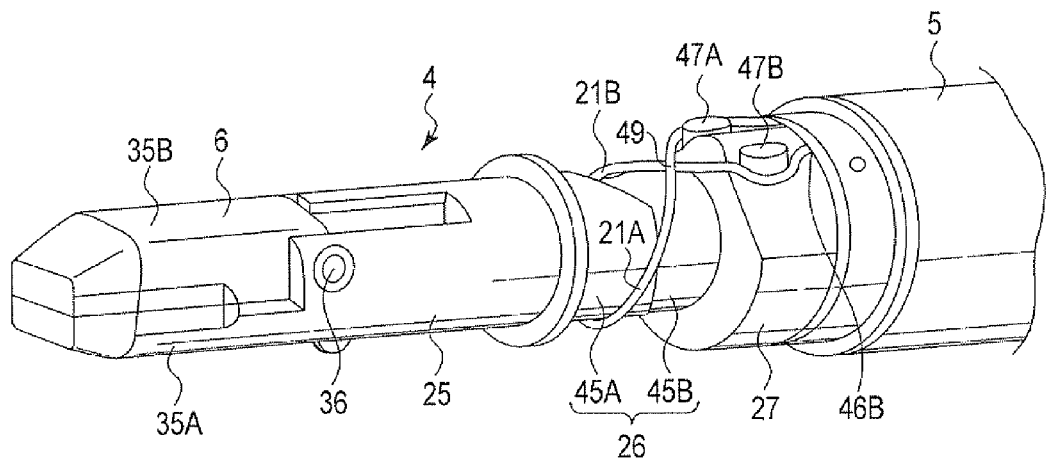
FIG. 5 is a perspective view schematically showing the distal direction side part of the treatment apparatus according to the first embodiment with the first cover and second cover being removed.
Figure 6:
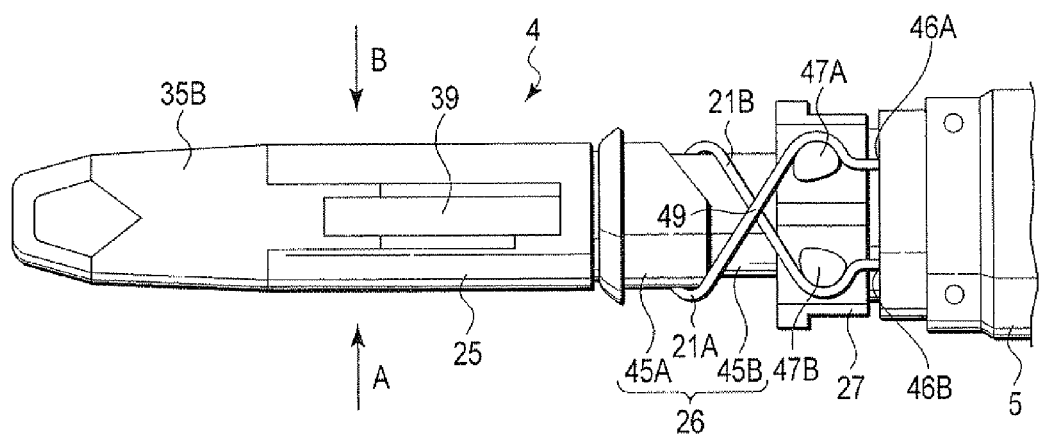
FIG. 6 is a plan view schematically showing the distal direction side part of the treatment apparatus according to the first embodiment with the first cover and second cover being removed.

As shown in FIGS. 5 and 6, the outer direction side of the rotor 26 is provided with a wire intersecting portion 49 in which the first rotating operation wire 21A intersects the second rotating operation wire 21B. That is, the wire intersecting portion 49 is provided between the wire fixing portion 40 and the first convex portion 47A (second convex portion 47B). As shown in FIG. 11, the second distance d2 from the longitudinal directions axis C of the flexible tube section 5 to the second outer surface 45B in the radial directions is smaller than the first distance d1 from the longitudinal directions axis C of the flexible tube section 5 to the first outer surface 45A in the radial directions. For this reason, in the wire intersecting portion 49, the first rotating operation wire 21A intersects the second rotating operation wire 21B while the first rotating operation wire 21A is located on the outer direction side, and the second rotating operation wire 21B is located on an inner direction side. The difference (d1−d2) between the first distance d1 and the second distance d2 is preferably equal to or lager than the diameter of the second rotating operation wire 21B. This makes the first and second rotating operation wires 21A and 21B intersect each other without contact in the wire intersecting portion 49.

The function of the treatment apparatus 1 according to this embodiment will be described next. When rotating the distal treatment section 4 of the treatment apparatus 1 to the directions about the axis relative to the flexible tube section 5, the rotating operation handle 12 is rotated in one rotation direction. With this operation, the first rotating operation wire 21A is pulled and the second rotating operation wire 21B is loosened through the bevel gear 20. When the first rotating operation wire 21A is pulled, the distal treatment section 4 rotates in the first rotation direction, which is one rotation direction.

FIG. 12 is a view explaining the rotating movement of the distal treatment section 4 in the first rotation direction. The first rotating operation wire 21A extends to the first outer surface 45A of the rotor 26, between the wire fixing portion 40 and the first convex portion 47A, along the first oblique direction inclining from the longitudinal directions to the circumferential directions. In this case, the first oblique direction is a direction inclining from the longitudinal directions toward the first rotation direction. As shown in FIG. 12, when the first rotating operation wire 21A is pulled, a force F1 acts on the rotor 26 in the first oblique direction. The force F1 is decomposed into a force F1 cos θ1 in the longitudinal directions and a rotational force F1 sin θ1 in the first rotation direction (circumferential directions). The rotational force F1 sin θ1 rotates the rotor 26 in the first rotation direction. In this case, the treatment section main body 25 and the second clamping portion 35B (distal treatment section 4) rotate together with rotor 26 to the directions about the axis. In the above manner, the distal treatment section 4 and the rotor 26 rotate in the first rotation direction relative to the flexible tube section 5 and the rotor support member 27.

When the rotating operation handle 12 is rotated in the other rotation direction, the first rotating operation wire 21A is loosened and the second rotating operation wire 21B is pulled through the bevel gear 20. Pulling the second rotating operation wire 21B will rotate the distal treatment section 4 in the second rotation direction opposite to the first rotation direction. FIG. 13 is a view explaining the rotating movement of the distal treatment section 4 in the second rotation direction. The second rotating operation wire 21B extends to the second outer surface 45B of the rotor 26, between the wire fixing portion 40 and the second convex portion 47B, along the second oblique direction inclining from the longitudinal directions to the circumferential directions. In this case, the second oblique direction is a direction inclining from the longitudinal directions toward the second rotation direction. As shown in FIG. 13, when the second rotating operation wire 21B is pulled, a force F2 acts on the rotor 26 in the second oblique direction. The force F2 is decomposed into a force F2 cos θ2 in the longitudinal directions and a rotational force F2 sin θ2 in the second rotation direction (circumferential directions). The rotational force F2 sin θ2 rotates the rotor 26 in the second rotation direction. At this time, the treatment section main body 25 and the second clamping portion 35B (distal treatment section 4) rotate together with the rotor 26 to the directions about the axis. In the above manner, the distal treatment section 4 and the rotor 26 rotate in the second rotation direction relative to the flexible tube section 5 and the rotor support member 27.

The treatment apparatus 1 is provided with the wire intersecting portion 49, between the wire fixing portion 40 to the outer direction side of the rotor 26 and the first convex portion 47A (second convex portion 47B), in which the first rotating operation wire 21A intersects the second rotating operation wire 21B. Providing the wire intersecting portion 49 will make the distal treatment section 4 rotate in the range of ±180° from the neutral position (initial position) when the distal treatment section 4 rotates to the directions about the axis relative to the flexible tube section 5.

In the treatment apparatus 1, the first distance d1 from the longitudinal directions axis C of the flexible tube section 5 to the first outer surface 45A of the rotor 26 is larger than the second distance d2 from the longitudinal directions axis C of the flexible tube section 5 to the second outer surface 45B of the rotor 26. In this case, setting the difference (d1−d2) between the first distance d1 and the second distance d2 to be equal to or larger than the diameter of the second rotating operation wire 21B makes the first and second rotating operation wires 21A and 21B intersect each other without contact in the wire intersecting portion 49. This reduces the influence of friction between the first rotating operation wire 21A and the second rotating operation wire 21B in the wire intersecting portion 49.

In addition, in the treatment apparatus 1, the first distance d1 from the longitudinal directions axis C of the flexible tube section 5 to the first outer surface 45A of the rotor 26 is larger than the second distance d2 from the longitudinal directions axis C of the flexible tube section 5 to the second outer surface 45B of the rotor 26. For this reason, when the rotational force F1 sin θ1 that rotates the distal treatment section 4 in the first rotation direction, is equal to the rotational force F2 sin θ2 that rotates the distal treatment section 4 in the second rotation direction, a rotational torque F1d1 sin θ1 in the first rotation direction becomes larger than a rotational torque F2d2 sin θ2 in the second rotation direction. In the treatment apparatus 1, the rotation direction in which the distal treatment section 4 is rotated at a high frequency, when, for example, performing a suturing operation by rotating the distal treatment section 4 while the grip portion 6 grips a needle, coincides with the first rotation direction. Increasing the rotational torque in the first rotation direction, in which the distal treatment section 4 rotates at a high frequency at the time of treatment, will improve the operability at the time of treatment with the distal treatment section 4. In this case, the first rotating operation wire 21A serves as a high-frequency pulling wire which is pulled at a higher frequency than the second rotating operation wire 21B.

The treatment apparatus 1 having the above configuration has the following effects. In the treatment apparatus 1 according to this embodiment, the first distance d1 from the longitudinal directions axis C of the flexible tube section 5 to the first outer surface 45A of the rotor 26 is larger than the second distance d2 from the longitudinal directions axis C of the flexible tube section 5 to the second outer surface 45B of the rotor 26. In this case, setting the difference (d1−d2) between the first distance d1 and the second distance d2 to be equal to or larger than the diameter of second rotating operation wire 21B makes the first and second rotating operation wires 21A and 21B intersect each other without contact in the wire intersecting portion 49. This reduces the influence of friction between the first rotating operation wire 21A and the second rotating operation wire 21B in the wire intersecting portion 49. This makes it possible to provide the treatment apparatus 1 which properly transfers rotating operation to the distal treatment section 4.

In addition, in the treatment apparatus 1, the first distance d1 from the longitudinal directions axis C of the flexible tube section 5 to the first outer surface 45A of the rotor 26 is larger than the second distance d2 from the longitudinal directions axis C of the flexible tube section 5 to the second outer surface 45B of the rotor 26. For this reason, when the rotational force F1 sin θ1 that rotates the distal treatment section 4 in the first rotation direction is equal to the rotational force F2 sin θ2 that rotates the distal treatment section 4 in the second rotation direction, the rotational torque F1$d$1 sin θ1 in the first rotation direction becomes larger than a rotational torque F2$d$2 sin θ2 in the second rotation direction. In the treatment apparatus 1, the rotation direction, in which the distal treatment section 4 is rotated at a high frequency at the time of treatment, coincides with the first rotation direction. Increasing the rotational torque in the first rotation direction, in which the distal treatment section 4 rotates at a high frequency at the time of treatment, will improve the operability at the time of treatment with the distal treatment section 4.

(Modification of First Embodiment)

A modification of the first embodiment will be described next with reference to FIGS. 14 to 16. The same reference numerals as in the first embodiment denote the same parts and parts having the same functions, and a description of them will be omitted.

FIG. 14 is a view showing the configuration of the treatment apparatus 1 according to the first modification of the first embodiment. As shown in FIG. 14, the operation section 51 of the treatment apparatus 1 is provided with a grip operation section 52 configured to perform the grip operation of gripping a tissue or the like with the grip portion 6. The grip operation section 52 includes a fixed handle 55 fixed to the operation section main body 10, and a movable handle 57 pivotably supported by the fixed handle 55 through a coupling pin 56. The movable handle 57 can pivot about the coupling pin 56 relative to the fixed handle 55. The proximal end of the grip operation wire 16 is connected to the movable handle 57. Pivoting the movable handle 57 in a direction to close relative to the fixed handle 55 will pull the grip operation wire 16. In addition, pivoting the movable handle 57 in a direction to open relative to the fixed handle 55 will loosen the grip operation wire 16.

The configuration of pulling or loosening the grip operation wire 16 according to the first modification is not limited to that of the embodiment described above. Likewise, the configuration of pulling or loosening the first and second rotating operation wires 21A and 21B is not limited to that of the above embodiment.

Figure 15:
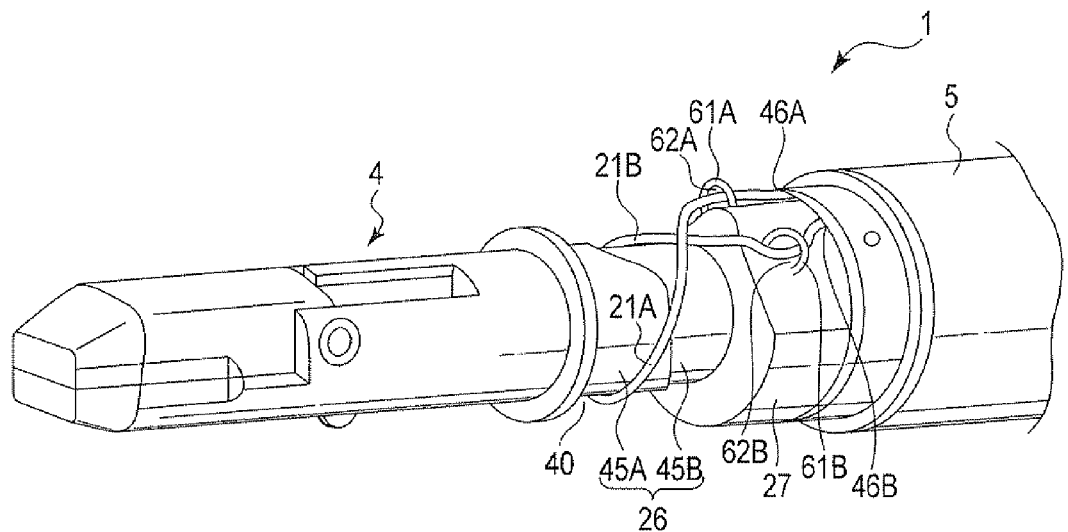
FIG. 15 is a perspective view schematically showing the distal direction side part of a treatment apparatus according to the second modification of the first embodiment.

FIG. 15 is a view showing the distal direction side part of the treatment apparatus 1 according to the second modification of the first embodiment. As shown in FIG. 15, the rotor support member 27 according to this modification is not provided with the first and second convex portions 47A and 47B. Instead of these parts, the rotor support member 27 is provided with a first guide portion 61A and a second guide portion 61B. The first guide portion 61A includes a first insertion hole 62A. The second guide portion 61B includes a second insertion hole 62B.

As shown in FIG. 15, the first rotating operation wire 21A, extending from the wire fixing portion 40, extends to the first outer surface 45A of the rotor 26 along the first oblique direction inclining from the longitudinal directions to the first rotation direction. The first rotating operation wire 21A extends through the first insertion hole 62A of the first guide portion 61A. Inserting the first rotating operation wire 21A into the first insertion hole 62A of the first guide portion 61A will change the extending direction of the first rotating operation wire 21A from the first oblique direction. The first rotating operation wire 21A, whose extending direction has been changed from the first oblique direction by the first guide portion 61A, is inserted from the first hole portion 46A into the flexible tube section 5. The first rotating operation wire 21A, which has been inserted into the flexible tube section 5, extends to the rotating operation section (rotating operation handle 12).

The second rotating operation wire 21B, extending from the wire fixing portion 40, extends to the second outer surface 45B of the rotor 26 along the second oblique direction inclining from the longitudinal directions to the second rotation direction. The second rotating operation wire 21B then extends through the second insertion hole 62B of the second guide portion 61B. Making the second rotating operation wire 21B extend through the second insertion hole 62B of the second guide portion 61B changes the extending direction of the second rotating operation wire 21B from the second oblique direction. The second rotating operation wire 21B, whose extending direction has been changed from the second oblique direction by the second guide portion 61B, is inserted from the second hole portion 46B into the flexible tube section 5. The second rotating operation wire 21B, which has been inserted into the flexible tube section 5, extends to the rotating operation section (rotating operation handle 12).

Figure 16:
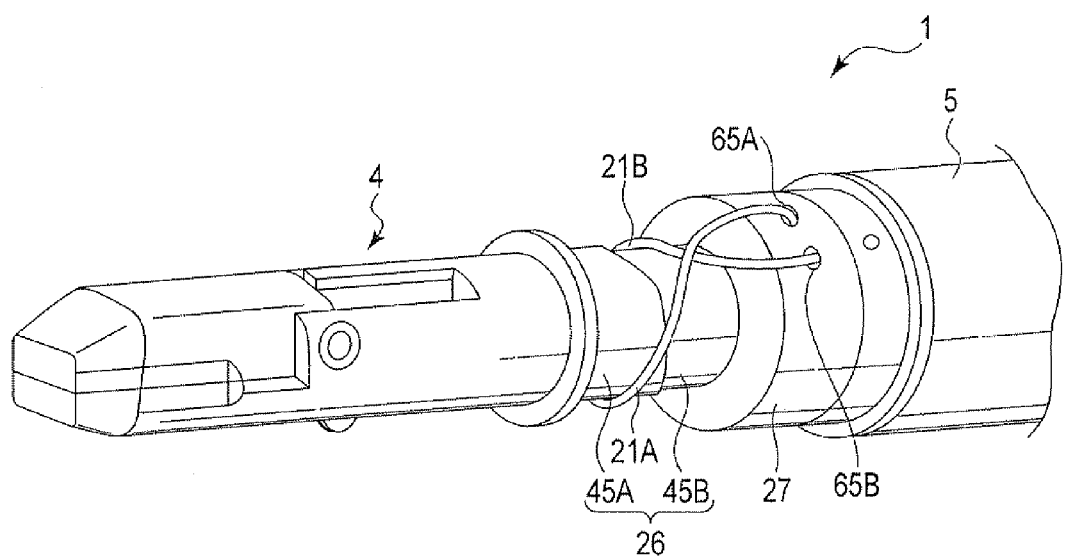
FIG. 16 is a perspective view schematically showing the distal direction side part of a treatment apparatus according to the third modification of the first embodiment.

FIG. 16 is a view showing the distal direction side part of the treatment apparatus 1 according to the third modification of the first embodiment. As shown in FIG. 16, the rotor support member 27 of this modification is not provided with the first and second convex portions 47A and 47B. Instead of these parts, the rotor support member 27 is provided with a first hole portion 65A and a second hole portion 65B.

As shown in FIG. 16, the first rotating operation wire 21A, extending from the wire fixing portion 40, extends to the first outer surface 45A of the rotor 26 along the first oblique direction inclining from the longitudinal directions to the first rotation direction. The first rotating operation wire 21A then extends through the first hole portion 65A of the rotor support member 27. Making the first rotating operation wire 21A extend through the first hole portion 65A changes the extending direction of the first rotating operation wire 21A from the first oblique direction. In addition, the first rotating operation wire 21A is inserted from the first hole portion 65A into the flexible tube section 5. The first rotating operation wire 21A, which has been inserted into the flexible tube section 5, extends to the rotating operation section (rotating operation handle 12).

The second rotating operation wire 21B, extending from the wire fixing portion 40, extends to the second outer surface 45B of the rotor 26 along the second oblique direction inclining from the longitudinal directions to the second rotation direction. The second rotating operation wire 21B then extends through the second hole portion 65B of the rotor support member 27. Making the second rotating operation wire 21B extend through the second hole portion 65B will change the extending direction of the second rotating operation wire 21B from the second oblique direction. The second rotating operation wire 21B is inserted from the second hole portion 65B into the flexible tube section 5. The second rotating operation wire 21B, which has been inserted into the flexible tube section 5, extends to the rotating operation section (rotating operation handle 12).

According to the second and third modifications, the configuration of changing the extending direction of the first rotating operation wire 21A from the first oblique direction and the configuration of changing the extending direction of the second rotating operation wire 21B from the second oblique direction are not limited those in the above embodiment. That is, this apparatus may be provided with a direction changing portion which is configured to change, from the first oblique direction, the extending direction of the first rotating operation wire 21A, which extends from the wire fixing portion 40 to the first outer surface 45A of the rotor 26 along the first oblique direction, and configured to make the first rotating operation wire 21A extend to the rotating operation section. Likewise, the apparatus may be provided with a direction changing portion which is configured to change, from the second oblique direction, the extending direction of the second rotating operation wire 21B, which extends from the wire fixing portion 40 to the second outer surface 45B of the rotor 26 along the second oblique direction, and configured to make the second rotating operation wire 21B extend to the rotating operation section.

In addition, the first and second convex portions 47A and 47B may be provided on a distal direction side part of the flexible tube section 5. That is, the first and second convex portions 47A and 47B may be provided on the distal direction side part of the flexible tube section 5 or a different member such as the rotor support member 27 provided between the flexible tube section 5 and the distal treatment section 4 while being fixed to the flexible tube section 5.

Furthermore, according to the above embodiment, the distal treatment section 4 and the rotor 26 are different members. However, they may be formed integrally. That is, the distal treatment section 4 and the rotor 26 may be configured to rotate to the directions about the axis relative to the flexible tube section 5. The wire fixing portion 40, to which the distal ends of the first and second rotating operation wires 21A and 21B are fixed, may be provided to the rotor 26 or a portion to the distal direction side of the rotor. In the above embodiment, the distal treatment section 4 includes the grip portion 6. However, the embodiment is not limited to this. For example, the distal treatment section 4 may be an electric scalpel.

(Second Embodiment)

The second embodiment of the present invention will be described next with reference to FIG. 17. Note that the same reference numerals as in the first embodiment denote the same parts and parts having the same functions, and a description of them will be omitted.

FIG. 17 is a view showing the configuration of the distal direction side part of a treatment apparatus 1 according to this embodiment. As shown in FIG. 17, a rotor 26 of this embodiment, as in the first embodiment, includes a first outer surface 45A and a second outer surface 45B. A first distance d1 from a longitudinal directions axis C of a flexible tube section 5 to the first outer surface 45A of the rotor 26 is larger than a second distance d2 from the longitudinal directions axis C of the flexible tube section 5 to the second outer surface 45B of the rotor 26.

A rotor support member 27 includes a member main body 71, and a protruding portion 72 which protrudes from the member main body 71 in the distal direction. The protruding portion 72 of the rotor support member 27 is provided with a second convex portion 47B. The member main body 71 of the rotor support member 27 is provided with a first convex portion 47A. That is, the second convex portion (second direction changing portion) 47B is provided to the distal direction side of the first convex portion (first direction changing portion) 47A.

A first rotating operation wire 21A extends on the first outer surface 45A of the rotor 26 along the first oblique direction. When the first rotating operation wire 21A abuts against the first convex portion 47A, the extending direction is changed from the first oblique direction. The first rotating operation wire 21A extends to a rotating operation section (rotating operation handle 12) through the flexible tube section 5. A second rotating operation wire 21B extends on the second outer surface 45B of the rotor 26 along the second oblique direction. When the second rotating operation wire 21B abuts against the second convex portion 47B, the extending direction is changed from the second oblique direction. The second rotating operation wire 21B then extends to the rotating operation section (rotating operation handle 12) through the protruding portion 72 of the rotor support member 27 and the flexible tube section 5.

As described above, the second convex portion 47B is provided to the distal direction side of the first convex portion 47A. The positions of the first and second convex portions 47A and 47B are adjusted to make a first angle θ1 between the longitudinal directions and the first oblique direction coincide with a second angle θ2 between the longitudinal directions and the second oblique direction. That is, the second convex portion 47B is provided at a position spaced apart from the first convex portion 47A by a predetermined distance L0 in the distal direction so as to make the first angle θ1 between the longitudinal directions and the first oblique direction coincide with the second angle θ2 between the longitudinal directions and the second oblique direction.

As described above in the first embodiment, when the first rotating operation wire 21A is pulled, a force F1 acts on the rotor 26 in the first oblique direction. With a rotational force F1 sin θ1, the rotor 26 rotates in the first rotation direction. Likewise, when the second rotating operation wire 21B is pulled, a force F2 acts on the rotor 26 in the second oblique direction. With a rotational force F2 sin θ2, the rotor 26 rotates in the second rotation direction. In this embodiment, the first angle θ1 between the first oblique direction and the longitudinal directions coincides with the second angle θ2 between the second oblique direction and the longitudinal directions. For this reason, when F1=F2, that is, the pulling force of the first rotating operation wire 21A coincides with that of the second rotating operation wire 21B, the rotational force F1 sin θ1 coincides with the rotational force F2 sin θ2. If, therefore, the pulling force of the first rotating operation wire 21A coincides with that of the second rotating operation wire 21B, the amount of rotation of the distal treatment section 4 to the first rotation direction coincides with that to the second rotation direction.

The treatment apparatus 1 having the above arrangement therefore has the following effects in addition to the effects of the first embodiment. That is, in the treatment apparatus 1 according to the second embodiment, the first convex portion 47A is spaced apart from the second convex portion 47B by the predetermined distance L0 in the distal direction, and the first angle θ1 between the first oblique direction and the longitudinal directions coincides with the second angle θ2 between the second oblique direction and the longitudinal directions. For this reason, if the pulling force of the first rotating operation wire 21A coincides with that of the second rotating operation wire 21B, the rotational force F1 sin θ1 coincides with the rotational force F2 sin θ2. Therefore, if the pulling force of the first rotating operation wire 21A coincides with that of the second rotating operation wire 21B, the amount of rotation of the distal treatment section 4 to the first rotation direction coincides with that to the second rotation direction. This makes it possible to improve the operability in the rotating operation of the distal treatment section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment apparatus comprising:
a flexible tube section which has a longitudinal directions axis and extends in longitudinal directions;
a distal treatment section which is provided to a distal direction side of the flexible tube section, and which is configured to rotate to directions about the longitudinal directions axis relative to the flexible tube section;
a rotating operation section which is provided to a proximal direction side of the flexible tube section, and which is configured to perform rotating operation of the distal treatment section;
a rotor which is fixed to the distal treatment section between the distal treatment section and the flexible tube section, and which is configured to rotate to the directions about the longitudinal directions axis relative to the flexible tube section, the rotor including a first outer surface spaced apart from the longitudinal directions axis of the flexible tube section by a first distance in radial directions, and a second outer surface spaced apart from the longitudinal directions axis of the flexible tube section by a second distance smaller than the first distance in the radial directions;
a wire fixing portion which is provided to the rotor or a portion to the distal direction side of the rotor;
a first rotating operation wire which has a distal end fixed to the wire fixing portion and extends from the wire fixing portion to the first outer surface of the rotor, the first rotating operation wire extending on the first outer surface in a state that the first rotating operation wire does not contact with the second outer surface, the first rotating operation wire being configured to be moved in an extending direction by the rotating operation in the rotating operation section so that a rotational force is applied from the first rotating operation wire to the first outer surface of the rotor toward a first rotation direction that is one of the directions about the longitudinal directions axis, and thereby the distal treatment section and the rotor being rotated in the first rotation direction by the rotational force applied from the first rotating operation wire;
a second rotating operation wire which has a distal end fixed to the wire fixing portion and extends from the wire fixing portion to the second outer surface of the rotor, the second rotating operation wire extending on the second outer surface in a state that the second rotating operation wire does not contact with the first outer surface, the second rotating operation wire being configured to be moved in an extending direction by the rotating operation in the rotating operation section so that a rotational force is applied from the second rotating operation wire to the second outer surface of the rotor toward a second rotation direction opposite to the first rotation direction, and thereby the distal treatment section and the rotor being rotated in the second rotation direction; and
a wire intersecting portion in which the first rotating operation wire and the second rotating operation wire intersect each other at positions apart from each other in a state that the second rotating operation wire is located on an inner direction side of the first rotating operation wire, wherein the first rotating operation wire and the second rotating operation wire are not in contact with each other.

2. The treatment apparatus of claim 1, wherein
the first rotating operation wire extends on the first outer surface along a first oblique direction inclining from the longitudinal directions to the first rotation direction, and
the second rotating operation wire extends on the second outer surface along a second oblique direction inclining from the longitudinal directions to the second rotation direction.

3. The treatment apparatus of claim 2, further comprising:
a first direction changing portion which is configured to change the extending direction of the first rotating operation wire from the first oblique direction, and configured to make the first rotating operation wire extend to the rotating operation section; and
a second direction changing portion which is configured to change the extending direction of the second rotating operation wire from the second oblique direction, and configured to make the second rotating operation wire extend to the rotating operation section.

4. The treatment apparatus of claim 3, wherein the second direction changing portion is provided to the distal direction side of the first direction changing portion.

5. The treatment apparatus of claim 4, wherein the second direction changing portion is spaced apart from the first direction changing portion by a predetermined distance in the distal direction so as to be located at a position where a first angle between the first oblique direction and the longitudinal directions coincides with a second angle between the second oblique direction and the longitudinal directions.

6. The treatment apparatus of claim 1, wherein a difference between the first distance and the second distance in the rotor is configured to be equal to or more than a diameter of the second rotating operation wire.

* * * * *